US005479943A

United States Patent [19]

Kuhnell, III

[11] Patent Number: 5,479,943

[45] Date of Patent: Jan. 2, 1996

[54] HANDCUFF SHIELD

[76] Inventor: John S. Kuhnell, III, 3204 Singletary, Apartment 159, Baker, La. 70714-2358

[21] Appl. No.: 430,577

[22] Filed: Apr. 28, 1995

[51] Int. Cl.$^{6}$ .............................. A61F 5/37; E05B 75/00

[52] U.S. Cl. .............................. 128/846; 128/878; 70/16

[58] Field of Search .................................... 128/845, 846, 128/869, 877, 878, 879; 2/16, 162, 170; 70/15, 16, 17, 18; 446/26; 602/20, 21

[56] References Cited

U.S. PATENT DOCUMENTS

| | | | |
|---|---|---|---|
| 2,679,842 | 6/1954 | Brill | 128/134 |
| 2,991,785 | 7/1961 | Terrell | 128/134 |
| 3,027,895 | 4/1962 | Williams | 128/133 |
| 4,299,213 | 11/1981 | Violet | 128/133 |
| 4,526,165 | 7/1985 | Mielnik, Jr. et al. | 128/133 |
| 4,977,625 | 12/1990 | Charters, III | 602/21 |
| 5,031,641 | 7/1991 | Upton | 128/878 |
| 5,138,852 | 8/1992 | Corcoran | 70/16 |
| 5,193,365 | 3/1993 | Nelson | 70/16 |
| 5,230,351 | 7/1993 | Nyorkor | 128/878 |

*Primary Examiner*—Michael A. Brown
*Attorney, Agent, or Firm*—David L. Ray

[57] ABSTRACT

A handcuff shield for covering a pair of handcuffs to prevent the handcuffs from touching the skin of the user and transmitting viruses and bacteria from the handcuff to the user, each of the pair of handcuffs being covered by the handcuff shield having an arcuate casing and an arcuate blade pivotally connected thereto for encircling a wrist of a person to whom the handcuffs are attached, the arcuate blade being receivable and lockable in the casing, the handcuff shield including a first body section having a bottom and two sidewalls extending upwardly therefrom for covering the arcuate casing, a second body section having a bottom and two sidewalls extending upwardly therefrom for covering the arcuate blade, and a flexible joint connecting the first body section to the second body section.

20 Claims, 1 Drawing Sheet

HANDCUFF SHIELD

BACKGROUND OF THE INVENTION

1. Field of the Invention

The invention relates to handcuffs. More particularly, the present invention relates to devices for preventing handcuffs from injuring the individual upon whom the handcuffs are placed.

2. Description of the Related Art

Persons being restrained with handcuffs may have cuts or scratches on their wrists prior to being handcuffed, and sometimes the handcuffs will cause cuts or breaks in the skin which result in blood being deposited on the handcuffs. If the handcuffs are not sterilized in an autoclave or chemically, the next person on whom the handcuffs are placed may contact the blood on the handcuffs and be exposed to any disease carried in the blood on the handcuffs. Such exposure is particularly dangerous because persons being restrained with handcuffs may have cuts or scratches on their wrists prior to being handcuffed, and sometimes the handcuffs will cause cuts or breaks in the skin which may contact the blood on the handcuffs from the previous person handcuffed.

Jails and prisons commonly use handcuffs on many prisoners on a daily basis, and the risk of infection is greater due to the many prisoners handcuffed daily by a single set of handcuffs. Infectious diseases carried by blood include AIDS (acquired immune deficiency syndrome) and other diseases which may result in the death or other disability of the inmate, and great pain and suffering over a long period of time. In addition, treatment for blood-born diseases contracted by inmates must be paid for by the governmental body which funds the jail or prison in which the inmates are incarcerated. Such treatment is commonly a significant financial burden for jails and prisons.

Exemplary of the Patents of the related art are the following U.S. Pat. Nos. 5,138,852; 4,526,165; 4,299,213; 3,027,895; 2,991,785; and 2,679,842.

SUMMARY OF THE INVENTION

In accordance with the present invention there is provided a handcuff shield for covering a pair of handcuffs to prevent the handcuffs from touching the skin of the user and transmitting viruses and bacteria from the handcuff to the user, each of the pair of handcuffs being covered by the handcuff shield having an arcuate casing and an arcuate blade pivotally connected thereto for encircling a wrist of a person to whom the handcuffs are attached, the arcuate blade being receivable and lockable in the casing, the handcuff shield including a first body section having a bottom and two sidewalls extending upwardly therefrom for covering the arcuate casing, a second body section having a bottom and two sidewalls extending upwardly therefrom for covering the arcuate blade, and a flexible joint connecting the first body section to the second body section.

The invention has the advantage of being easily placed on a pair of conventional handcuffs to decrease the risk on transmitting viruses and bacteria from handcuffs to the person wearing the handcuffs.

The invention also has the advantage of being low in cost.

The invention has the further advantage of being easily disposable after use.

DESCRIPTION OF THE PREFERRED EMBODIMENTS

Figure 1:
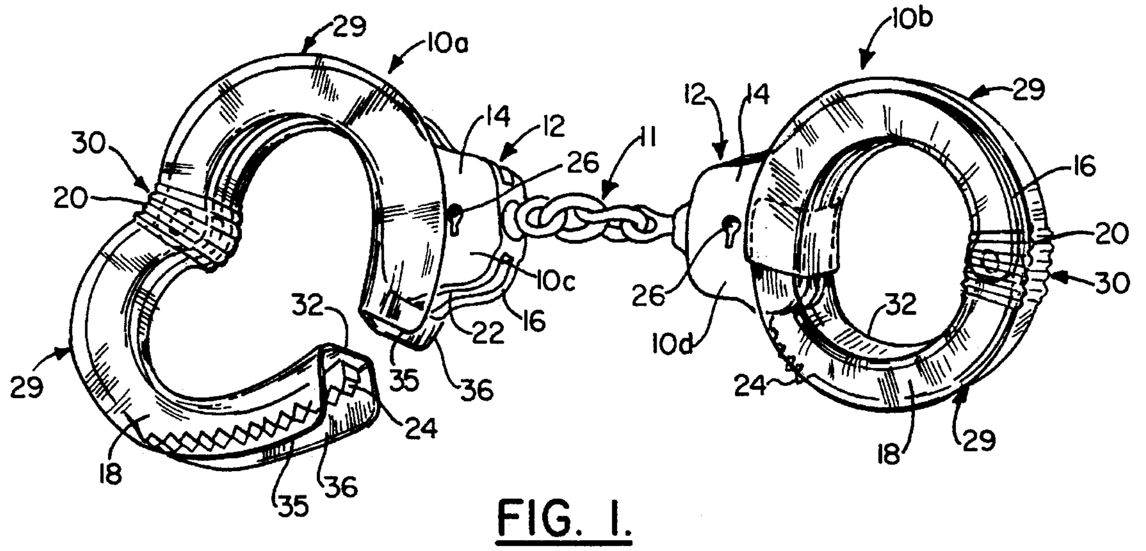
FIG. 1 is a perspective view of a set of handcuffs have the shield of the invention placed thereon.

Referring now to the drawings, in FIG. 1 is shown a matching pair of exemplary handcuffs generally indicated by the numerals **10*a* and 10*b*. Handcuffs 10*a* and 10*b* may be any handcuffs known in the art such as the handcuffs disclosed in U.S. Pat. No. 5,138,852 which is hereby incorporated by reference. Handcuff 10*a* is connected to handcuff 10*b* by the chain generally indicated by the numeral 11. Each exemplary handcuff 10*a* and 10*b* includes a casing 12 having a lock (not shown) therein and a pair of arcuate spaced-apart cheek plates 14 and 16 preferably integrally formed therewith, and an arcuate blade 18 connected by a pivot pin 20 to the cheek plates 14 and 16. Blade 18 is traversable through a channel 22 defined by the casing 12. The lock (not shown) may be identical to the lock shown in U.S. Pat. No. 5,138,852 which has been incorporated by reference. A plurality of teeth 24 are located on the outer edge and outer end of each blade 18 for locking receipt in channel 22 of casing 12 as shown in handcuff 10*b*. Handcuffs 10*a* and 10*b* each have a keyhole 26 in the casing 12 for receiving a key (not shown) to open the lock (not shown) in casing 12** to unlock the handcuffs when they are locked.

Figure 2:
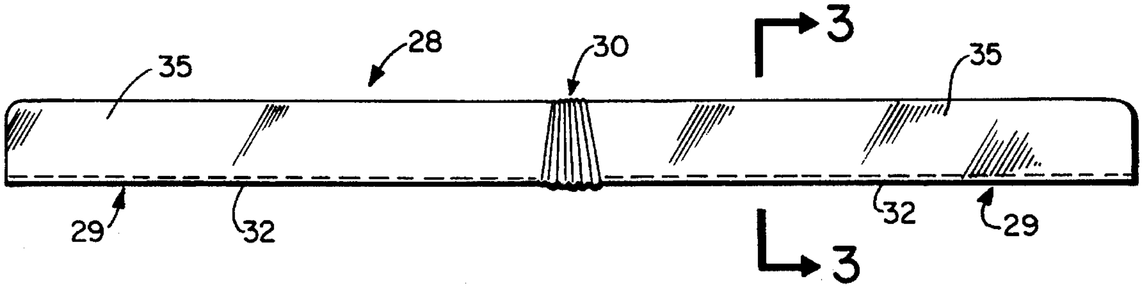
FIG. 2 is a side, elevation view of a shield of the invention.

The shield of the invention is generally indicated by the numeral 28 in FIG. 2. Shield 28 is preferably integrally formed from a single material. Preferably, shield 28 is molded from a flexible plastic or synthetic rubber material such as the material used to make surgical gloves which is impervious to the transmission of viruses and bacteria. Shield 28 is preferably transparent or translucent.

Figure 3:
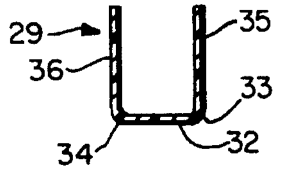
FIG. 3 is a cross sectional view taken along lines 3—3 of FIG. 2.

Shield 28 can be seen in FIGS. 2 and 3 to have two linear body sections generally indicated by the numerals 29—29 which are connected together by the flexible joint generally indicated by the numeral 30. Joint 30 preferably has a plurality of ridges and troughs as shown in the drawings similar to an accordion bellows. However, if desired, the plurality of ridges and troughs could be eliminated and joint 30 could be constructed of flat material such as the flat material from which body sections 29—29 are constructed.

Each of body sections 29—29 can be seen to have a generally rectangular bottom section 32 connected together by joint 30. Each bottom section lies in a single plane, and each body section is made from a flexible material that can be bent to conform to the arcuate shape of the handcuffs being shielded. As can best be seen in FIG. 3, extending upwardly from each edge 33 and 34 of each bottom section 32 are two generally rectangular, generally parallel sidewalls 35 and 36. Sidewalls 35—35 are connected together at one end by joint 30 and sidewalls 36—36 are connected together at one end by joint 30. Thus, the body sections 29—29 and joint 30 have a U-shaped cross-section.

Figure 4:
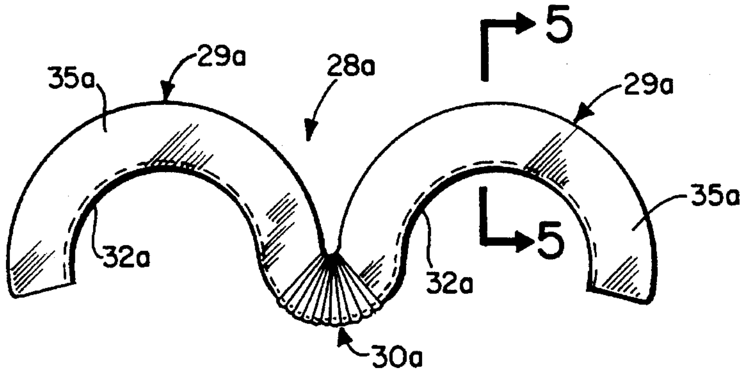
FIG. 4 is a side elevational view of a preferred embodiment of the shield of the invention.
Figure 5:
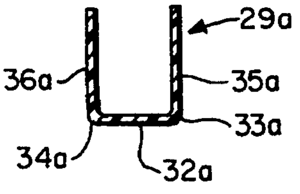
FIG. 5 is a cross-sectional view taken along lines 5—5 of FIG. 4.

In FIGS. 4 and 5 is shown a preferred embodiment of the shield of the invention generally indicated by the numeral **28*a*. Shield 28*a* can be seen in the drawings to have two arcuate body sections generally indicated by the numerals 29*a*–29*a* which are connected together by the flexible joint generally indicated by the numeral 30*a*. Joint 30*a* preferably has a plurality of ridges and troughs as shown in the drawings similar to an accordion bellows. However, if desired, the plurality of ridges and troughs could be eliminated and joint 30***a* could be constructed of flat material such as body sections 29*a*–29*a*.

Each of the body sections 29*a*–29*a* can be seen to have an arcuate bottom section 32*a* connected together by joint 30*a*. Extending upwardly from each edge 33*a* and 34*a* of each bottom section 32*a* are two generally parallel arcuate sidewalls 35*a* and 36*a*. Sidewalls 35*a*–35*a* are connected together at one end by joint 30*a* and sidewalls 36*a*–36*a* are connected together at one end by joint 30*a*. Thus, the body sections 29*a*–29*a* and joint 30*a* have a U-shaped cross-section.

As can be seen in FIG. 1, one of the body sections 29 fits over handcuff blade 18 and the other body section 29 connected thereto fits over cheek plates 14 and 16, with the bottom section 32 being oriented inside of the handcuff to contact the wrist of the person on whom the handcuffs are placed. Similarly, one of the body sections 29*a* fits over handcuff blade 18 and the other body section 29*a* connected thereto fits over cheek plates 14 and 16, with the bottom section 32*a* being oriented inside of the handcuff to contact the wrist of the person on whom the handcuffs are placed. Flexible joints 30 as shown in FIG. 1 and 30*a* have a U-shaped cross-section for quick and easy placement over pivot pin 20 of handcuffs 10*a* and 10*b*.

Thus, the wrists of the person on whom handcuffs utilizing the shield of the invention are placed do not contact the handcuffs, and transmission of viruses and bacteria from the handcuffs to the wearer of the handcuffs is prevented. When the handcuffs are removed, the handcuff shields 28 or 28*a* are discarded and replaced with new handcuff shields. The handcuff shield of the invention can be quickly and easily placed on each handcuff by opening the handcuff and sliding the shield 28 or 28*a* thereon so that the bottom 32 or 32*a* is on the inside of casing 12 and blade 18, and the sidewalls 35 and 36, or sidewalls 35*a* and 36*a*, cover each side of casing 12 and blade 16. The handcuffs can then be placed on a person's wrists.

Handcuff shields 28 and 28*a* are constructed from inexpensive materials and can be disposed of at a cost negligible when compared to the increased risk of infection when not used.

Both handcuff shields 28 and 28*a* are sized to fit standard handcuffs. The embodiment shown in FIGS. 4 and 5 is preferred because the shield 28*a* may be more easily fitted onto a pair of handcuffs since it is pre-curved to conform to the curved portions of handcuffs.

Although the preferred embodiments of the invention have been described in detail above, it should be understood that the invention is in no sense limited thereby, and its scope is to be determined by that of the following claims:

What is claimed is:

1. A handcuff shield for covering a pair of handcuffs to prevent the handcuffs from touching the skin of the user and transmitting viruses and bacteria from the handcuff to the user, each of said pair of handcuffs being covered by said handcuff shield having an arcuate casing and an arcuate blade pivotally connected thereto for encircling a wrist of a person to whom the handcuffs are attached, said arcuate blade being receivable and lockable in said casing, said handcuff shield comprising:

a. first body section means having a bottom and two sidewalls extending upwardly therefrom for covering said arcuate casing, b. a second body section means having a bottom and two sidewalls extending upwardly therefrom for covering said arcuate blade, and c. a flexible joint means for connecting said first body section means to said second body section means.

2. The handcuff shield of claim 1 wherein said first body section means covers the inside and sides of said arcuate casing.

3. The handcuff shield of claim 1 wherein said first body section means has a U-shaped cross-section.

4. The handcuff shield of claim 2 wherein said first body section means covers the inside and sides of said arcuate blade.

5. The handcuff shield of claim 1 wherein said second body section means covers the inside and sides of said arcuate blade.

6. The handcuff shield of claim 1 wherein said second body section means has a U-shaped cross-section.

7. The handcuff shield of claim 6 wherein said second body section means covers the inside and sides of said arcuate blade.

8. The handcuff shield of claim 1 wherein said handcuff shield is made from a flexible material.

9. The handcuff shield of claim 8 wherein said handcuff shield is impervious to the transmission of viruses and bacteria.

10. The handcuff shield of claim 1 wherein said flexible joint means has a plurality of folds therein.

11. The handcuff shield of claim 1 wherein said flexible joint means has a generally U-shaped cross-section.

12. The handcuff shield of claim 11 wherein said flexible joint means has a plurality of folds therein.

13. The handcuff shield of claim 1 wherein said bottom of said first body section means and said second body section means lie in the same plane prior to placement upon each of said pair of handcuffs.

14. The handcuff shield of claim 1 wherein said bottom of said first body section means and said second body section means are arcuate.

15. A handcuff shield for covering a pair of handcuffs to prevent the handcuffs from touching the skin of the user and transmitting viruses and bacteria from the handcuff to the user, each of said pair of handcuffs being covered by said handcuff shield having an arcuate casing and an arcuate blade pivotally connected thereto for encircling a wrist of a person to whom the handcuffs are attached, said arcuate blade being receivable and lockable in said casing, said handcuff shield comprising:

a. first arcuate body section means having a bottom and two sidewalls extending upwardly therefrom for covering said arcuate casing, b. a second arcuate body section means having a bottom and two sidewalls extending upwardly therefrom for covering said arcuate blade, and c. a flexible joint means for connecting said first body section means to said second body section means.

16. The handcuff shield of claim 15 wherein said first arcuate body section means covers the inside and sides of said arcuate casing, said first body section means having a U-shaped cross-section, and said second arcuate body section means covers the inside and sides of said arcuate blade, said second body section means having a U-shaped cross-section.

17. The handcuff shield of claim 16 wherein said flexible joint means has a generally U-shaped cross-section.

18. A handcuff shield for covering a pair of handcuffs to prevent the handcuffs from touching the skin of the user and transmitting viruses and bacteria from the handcuff to the user, each of said pair of handcuffs being covered by said handcuff shield having an arcuate casing and an arcuate blade pivotally connected thereto for encircling a wrist of a person to whom the handcuffs are attached, said arcuate blade being receivable and lockable in said casing, said handcuff shield comprising:

a. a flexible first body section means having a bottom and two sidewalls extending upwardly therefrom for covering said arcuate casing, b. a flexible second body section means having a bottom and two sidewalls extending upwardly therefrom for covering said arcuate blade, and c. a flexible joint means for connecting said first body section means to said second body section means, said bottom of said first body section means and said bottom of said second body section means lying in the same plane prior to placement upon each of said pair of handcuffs.

19. The handcuff shield of claim 18 wherein said first body section means covers the inside and sides of said arcuate casing, said first body section means having a U-shaped cross-section, and said second body section means covers the inside and sides of said arcuate blade, said second body section means having a U-shaped cross-section.

20. The handcuff shield of claim 19 wherein said flexible joint means has a generally U-shaped cross-section.

* * * * *